United States Patent [19]
Nurse, Jr. et al.

[11] Patent Number: 6,006,612
[45] Date of Patent: Dec. 28, 1999

[54] WASTE WATER EFFLUENT TEST METHOD AND ASSEMBLY

[75] Inventors: Harry L. Nurse, Jr., 10409 Watterson Trail, Louisville, Ky. 40299; Lawrence E. Gravely, Louisville, Ky.

[73] Assignee: Harry L. Nurse, Jr., Louisville, Ky.

[21] Appl. No.: 08/929,779

[22] Filed: Sep. 15, 1997

[51] Int. Cl.[6] ............................... G01N 1/10; G01N 1/18
[52] U.S. Cl. ..................... 73/863.23; 73/863.31
[58] Field of Search .......................... 73/863.21, 863.23, 73/863.31, 863.41, 863.51, 863.52, 863.61, 863.83, 863.86, 864.34, 864.73

[56] References Cited

U.S. PATENT DOCUMENTS

| | | | |
|---|---|---|---|
| 3,765,247 | 10/1973 | Riggs | 73/863.23 |
| 4,090,392 | 5/1978 | Smith et al. | 73/863.23 |
| 4,517,849 | 5/1985 | Nakahori et al. | 73/863.31 |
| 5,161,417 | 11/1992 | Strong et al. | 73/863.66 |

*Primary Examiner*—Daniel S. Larkin
*Attorney, Agent, or Firm*—Middleton & Reutlinger; Charles G. Lamb

[57] ABSTRACT

A test assembly for permitting the sampling of the effluent of a waste water treatment apparatus is comprised of at least two parallel testing lines, one testing line being in flow communication with effluent that has been filtered through one type of filter and the second testing line being in flow communication with effluent that is unfiltered or has been filtered through a second type of filter. At least one positive shut-off valve is provided so each testing line can be shut off when effluent is passing through the other testing line.

18 Claims, 6 Drawing Sheets

WASTE WATER EFFLUENT TEST METHOD AND ASSEMBLY

BACKGROUND OF THE INVENTION

The present invention relates to a test assembly for allowing the sampling of waste water effluent and more particularly to a method for testing the performance of selected devices and apparatuses in waste water systems.

Waste water treating facilities, and particularly septic tanks, are used to provide economical waste disposal for residential and commercial facilities in areas which are not served by sewer lines leading to sewer treatment facilities. The incoming fluids into the tanks includes large solids which are digested in the tank or broken into smaller solids. The final treatment of septic tank sewage is therefore in the drain fields. However, it is desirable to prevent the flow of as much of these solid particulates as possible into the drain field and therefore filters are provided in the outlet waste water streams from the septic tanks into the drain fields. And, the efficiency of some of these filters have proved to be inadequate in view of the fact that many of these filters become clogged with small particulates or the openings in the filter media in the filters are sufficiently large that a large segment of particulate materials flows through the outlet into the drain field.

There have been a number of test procedures that help to determine the efficiency of these filters but in most cases they have proved to be inadequate and/or excessively time consuming in determining the filters' efficiency. Particularly, since the materials in the septic tank are generally separated into a number of layers, large particulates being in the lowermost layer, a relatively clear layer being in the middle, and the uppermost layer generally consists of light weight solids and foam floating on the upper most layer, effluent leaving the filter is generally in a relatively laminar flow and therefore is also layered in the outlet conduits as it flows from the inside of the septic tank into the drain fields. Thus, grab samples at any given time are generally inadequate in view of the fact that only one of the layers may be obtained in the grab sample. Moreover, there have been continuous 24 hour composite sampling machines devised to sample the flow of effluent from a septic tank, but such devices have proved to be extremely costly and time consuming. More importantly, in some of these continuous 24 hour composite sampling machines, the machines are connected up to a tube which is installed in the effluent discharge wherein the tube includes openings therethrough which acts as a filter or particle selection device, due to the small opening sizes, thereby providing incorrect and unreliable information. Also with the composite sampling tube openings being at a fixed level, and with a small orifice, again only one layer of the effluent exiting the tank is taken and the solids determination assumed to be representative of the total effluent flowing from the septic tank, is in error.

SUMMARY OF THE INVENTION

It is an object of the present invention to provide an accurate sampling device for permitting measured sample taking of the effluent from a waste water treatment system.

It is another object of the present invention to provide a waste water sampling device which is economical.

It is a further object of the present invention to provide a sampling device and method to sample 100% of the exiting effluent of a waste water treatment plant at any given sampling time.

It is also an object of the present invention to provide a waste water effluent sampling method which may be used to compare the efficiency of two or more different types of filters in a waste water treatment plant discharge simultaneously.

More particularly, the present invention provides a sampling assembly for waste water effluent comprising: a first flow line and a second flow line, each of the flow lines having an inlet in flow communication with a waste water effluent source, each of the flow lines having an outlet, at least one of the flow lines having a housing with filter means therein; a first testing means disposed within said first flow line, the first testing means having a first sample port with a first valve means disposed to close off flow to the first sample port; a second testing means disposed within said second flow line, said second testing means having a second sample port with a second valve means disposed to close off flow to the second sample port.

Even more particularly, the present invention provides a method for sampling waste water effluent comprising the steps of: (a) passing effluent through a first testing line including a first valve in an open condition into a first sample collection port; (b) closing the first valve; (c) removing all effluent from the first sample collection port; (d) opening the first valve for a preselected period of time; (e) closing said first valve; (f) removing all effluent from the first sample collection port; (g) opening a second valve in a second testing line; (h) passing effluent through said second testing line including said second valve into a second sample collection port; (i) closing the second valve; (j) removing all effluent from the second sample collection port; (k) opening the second valve for a preselected period of time; (l) closing said second valve; (m) removing all effluent from the second sample collection port; (n) opening said first valve; and, (o) determining selected physical and/or chemical properties such as solid concentrations, from the first sample collection port and from the second collection port and comparing results from said determining of physical and/or chemical properties.

In the use of the term waste water treatment herein, this includes both aerobic and anaerobic treatment plants, or mixed treatment plants, such as for example, septic tanks, and the like.

Further objects and advantages will occur to those skilled in the art upon reading the description of the preferred embodiments of the present invention set forth hereinafter.

DETAILED DESCRIPTION OF THE PREFERRED EMBODIMENT

Figure 1:
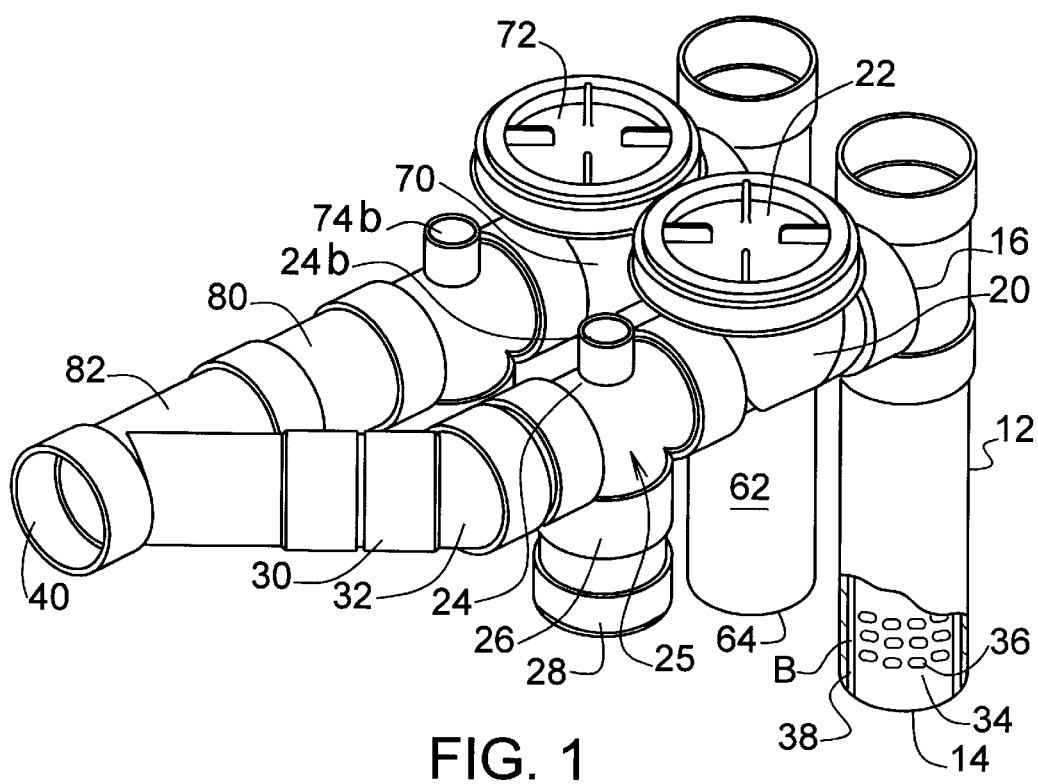
FIG. 1 is a perspective view of one test assembly of the present invention.
Figure 2:
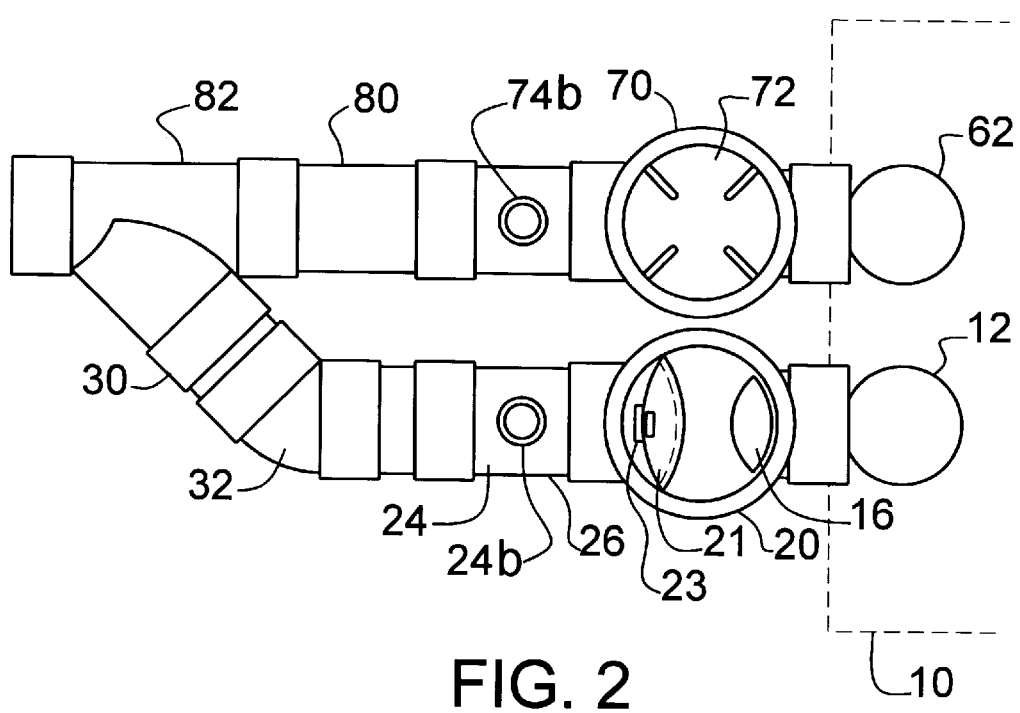
FIG. 2 is a top view of the test assembly of FIG. 1.
Figure 3:
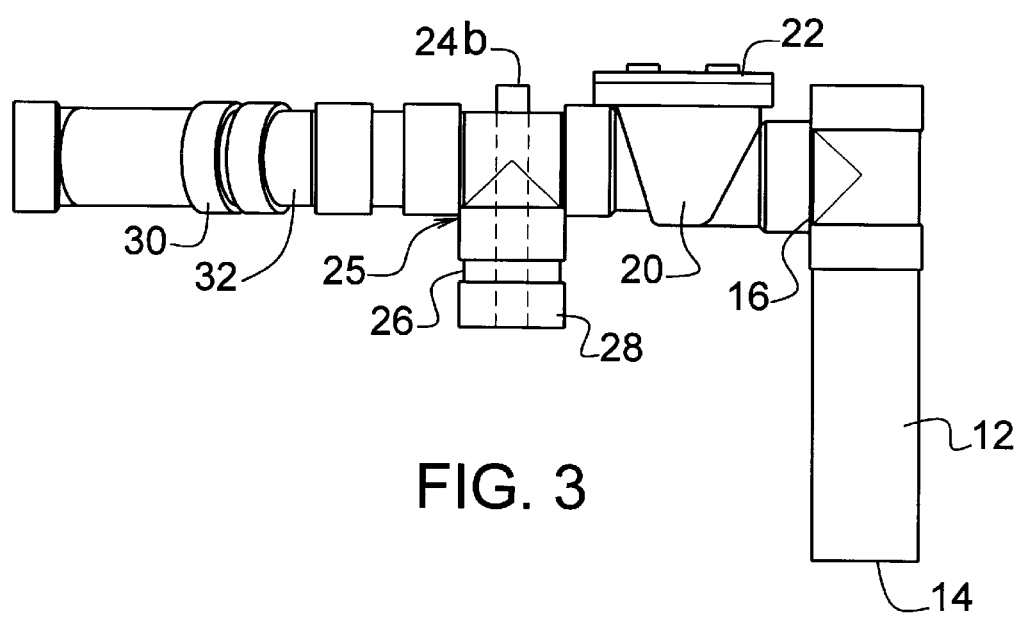
FIG. 3 is a side view of the test assembly of FIG. 1.

As shown in FIG. 1, a sample assembly of the present invention comprises a first testing line and a second testing line wherein at least one of the test lines includes a filter therein for removing particles greater than a preselected size such as, for example, ⅛' diameter, as opposed to a waste water treatment outlet which does not have a treatment device therein or includes a filter treatment device which is of a different type than that in the first testing line. In FIG. 1, the first testing line includes a first housing 12 having an inlet 14 and an outlet 16. The inlet 14 is in flow communication with a waste water treatment effluent and is generally disposed within a septic tank as shown in the phantom lines identified by the numeral 10 in FIG. 2. The first housing 12, as shown in a partially removed section, is provided with a slotted filter 34 having a central opening therein and a plurality of openings 36 disposed along the entire length of the tubular filter. Tubular filter 34 is spaced from the inner surface of housing 12 providing a chamber 38 between the outer surface of the tubular filter 34 and the inner surface of the housing 12 thereby providing a flow chamber for the filtered effluent, identified by the letter "B", which passes upwardly along the chamber 38 to the outlet 16. The outlet 16 is in flow communication with a sample collection port 25 with a valve 20 disposed therebetween. One preferred valve 20, as best shown in FIG. 2, is a back flow valve having a detachable flap plate 21 for closing off the flow of effluent through the first test line when the flap plate 21 is attached to the hinged assembly 23. When not in place, the flap plate 21 may be removed completely from the valve 20 thereby enabling full flow of the effluent through the first testing line. The valve 20 is provided with a valve cover 22 which is threadly received within the valve body of the valve 20.

The sample collection port 25 which includes a cover 24 with a sampling tube insertion opening 24b shown in an open condition but it is realized that in a non-use condition, a cap, not shown, may be provided over the opening. The sample collection port 25 further includes a sampling well identified by the numeral 26 which is closed off at the bottom with a cap 28. In use, a sampling tube, not shown, can be placed through the sampling tube opening 24b and inserted completely into the sampling well 26. The effluent contained within the sampling well is then removed generally by vacuum so that the entire contents of the sample collection port is removed.

The sample collection port 25 is in flow communication on its downstream side with the outlet 40 from the testing assembly. Between the sample collection port 25 and the outlet 40 is an elbow 32 and an outlet 30 which is in flow communication with a 45° tee identified by the numeral 82.

A second testing line is shown as including a second housing 62 having an inlet 64 in flow communication with the waste water effluent. The second housing 62 is provided with an inlet in flow communication with a second flow valve 70 having a cover 72 thereon. The valve 72 is generally the same valve as valve 22 shown in the first testing line. The valve 70 has an outlet in flow communication with the second sample collection port which is provided with a second port opening 74b therein to receive a sample tube (not shown) therethrough. The second sample collection port is substantially the same as the first sample collection port discussed previously. The second sample collection port is in flow communication with outlet 80 and in turn is in flow communication on its downstream end with one end of the 45° tee 82.

The housing 62 may include a second type of filter which is dissimilar from the filter 34 in the housing 12, or housing 62 may be completely open for receiving non-treated effluent from a waste water treatment tank.

The operation of the second testing line is essentially the same as the first testing line. If the second testing line is the control, that is, the line is not normally in use during normal operation, then valve 70 in the second testing line will be in a closed condition until a sample is ready to be taken, in which case, a flap plate in the valve will be removed thereby opening the flow of effluent into the sample collection port. After a preselected period of time, the flap plate will be replaced in the valve and all of the effluent contained within the sampling collection port, including the sampling well, is then removed. Once the second sample collection port has been evacuated, the flap plate is removed from the valve for the flow of effluent into the second sample collection port. After a selected period of time, the flap cover is removed and the flap plate is then reinserted to close off the effluent flow into the sample collection port. The procedure of evacuating all of the effluent from the sample collection port is repeated in order to obtain a sample of all of the effluent passing through the second testing line for the preselected period of time.

Figure 4:
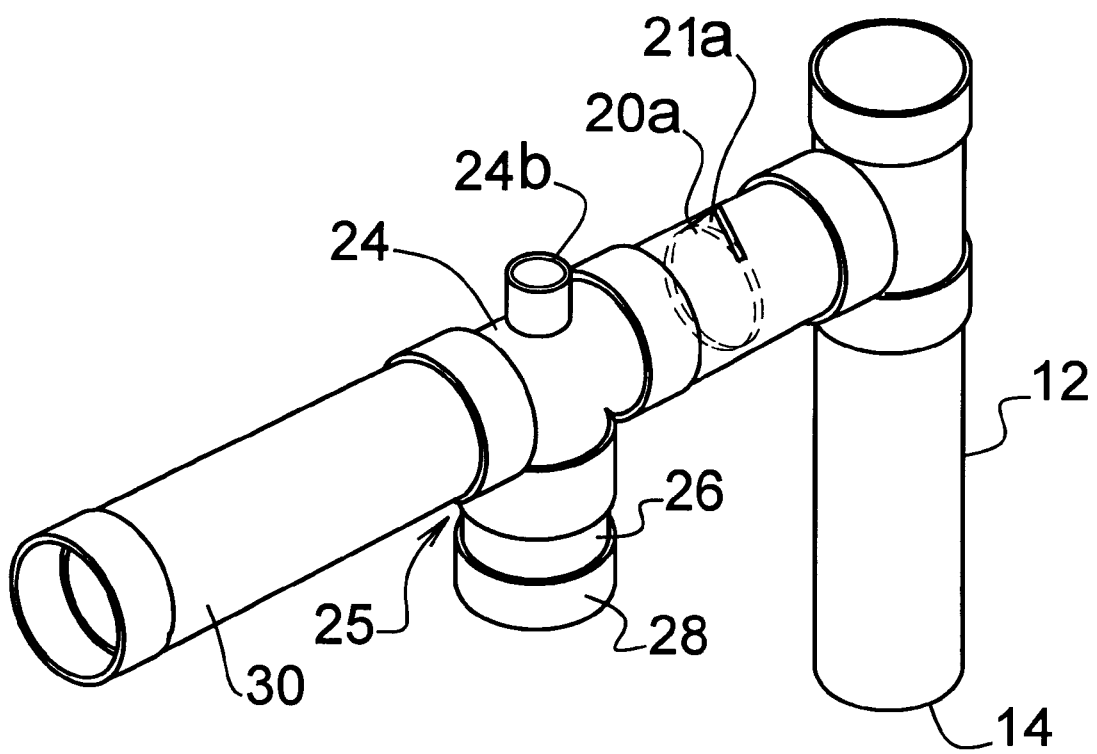
FIG. 4 is perspective view of another embodiment of a flow line of the test assembly of FIG. 1.

It is realized that many different types of valves may be utilized in the testing assembly of the present invention and in FIG. 4 a slide gate valve identified by the numeral 20a is provided with a slide gate identified by the numeral 21a being inserted therein. Other inexpensive valves may be utilized in the test system as long as the valve utilized is one which closes off the entire flow through the test line for the required period of time to evacuate all of the effluent from the sample collection port.

In the testing of an effluent discharging from a waste water treatment tank, as shown in FIGS. 1–4, which ever testing line is to be tested, the valve in that test line is closed and the cap (not shown) covering the sample port opening 24b, 74b is removed. The sample tube is then inserted into the sample port 24b or 74b and all of the effluent that is disposed within the sample collection port, exemplified by numeral 25, is then removed by vacuum means. In the use of a rigid sample tube, and in one particularly preferred embodiment, an Erlenmeyer vacuum flask (not shown) and sampling pump (not shown) which permits sample taking within 3–5 cm of the bottom of the well are used in taking a sample. After the sample collection port has been completely evacuated, the valve 20 or 70 is then opened and the effluent is allowed to pass therethrough for a preselected period time and then the valve 20 or 70 is closed back off to prevent the flow of effluent into the sample collection well. The sample tube is then reinserted into the sampling tube port opening 24b or 74b and again the sampling well is evacuated of all of the effluent therein and this sample is then saved for a solids concentration analysis to be determined later. The valve 20 or 70 is then reopened and the effluent is allowed to pass unobstructed through the particular testing line. The procedure is then repeated in the other testing line and the sample therefrom is then analyzed to determine, for example, the solids concentration in the effluent. Comparisons are then made between the solids concentration in the first testing line against the second testing line to determine either the efficiency of a particular filter against unfiltered effluent or of two different types of filters in the housings 12 and 62. Analyses of the samples will determine the efficiencies of the two different types of filters in relation to each other. Even though only two testing lines are shown, it is realized that there may be more than two testing lines in use in the present invention.

Figure 5:
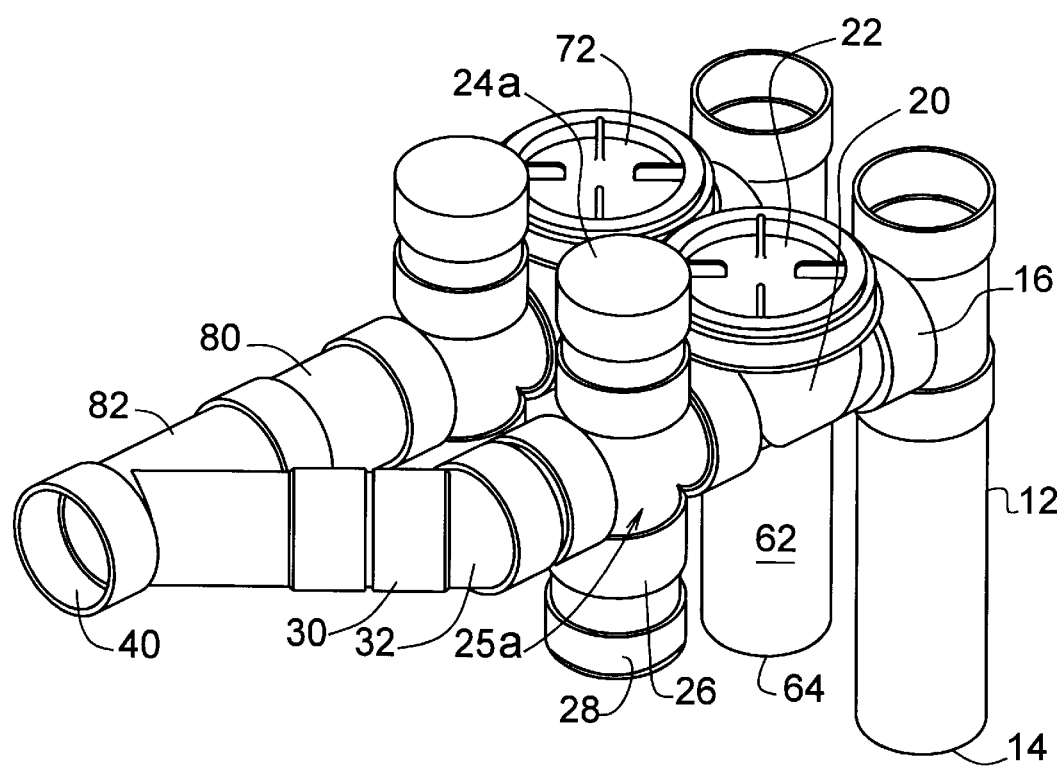
FIG. 5 is a perspective view of another test assembly of the present invention.
Figure 6:
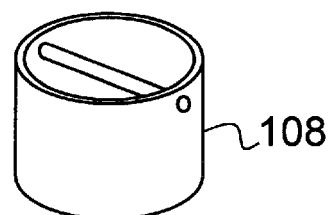
FIG. 6 is a perspective view of a cup for use with the test assembly shown in FIG. 5.

In FIG. 5 is shown another preferred test assembly of the present invention wherein the distinction between the embodiment of FIG. 5 and FIGS. 1–4 is in the sample collection port identified by the numeral 25a in FIG. 5. In this particular embodiment, the cover 24 is replaced by a cap 24a whereby the entire sample well can be evacuated with the use of a vacuum and used as a sample. Moreover, as shown in FIG. 6, a sample cup 108 may be received within the sample wells and used instead of a sample tube.

Figure 7:
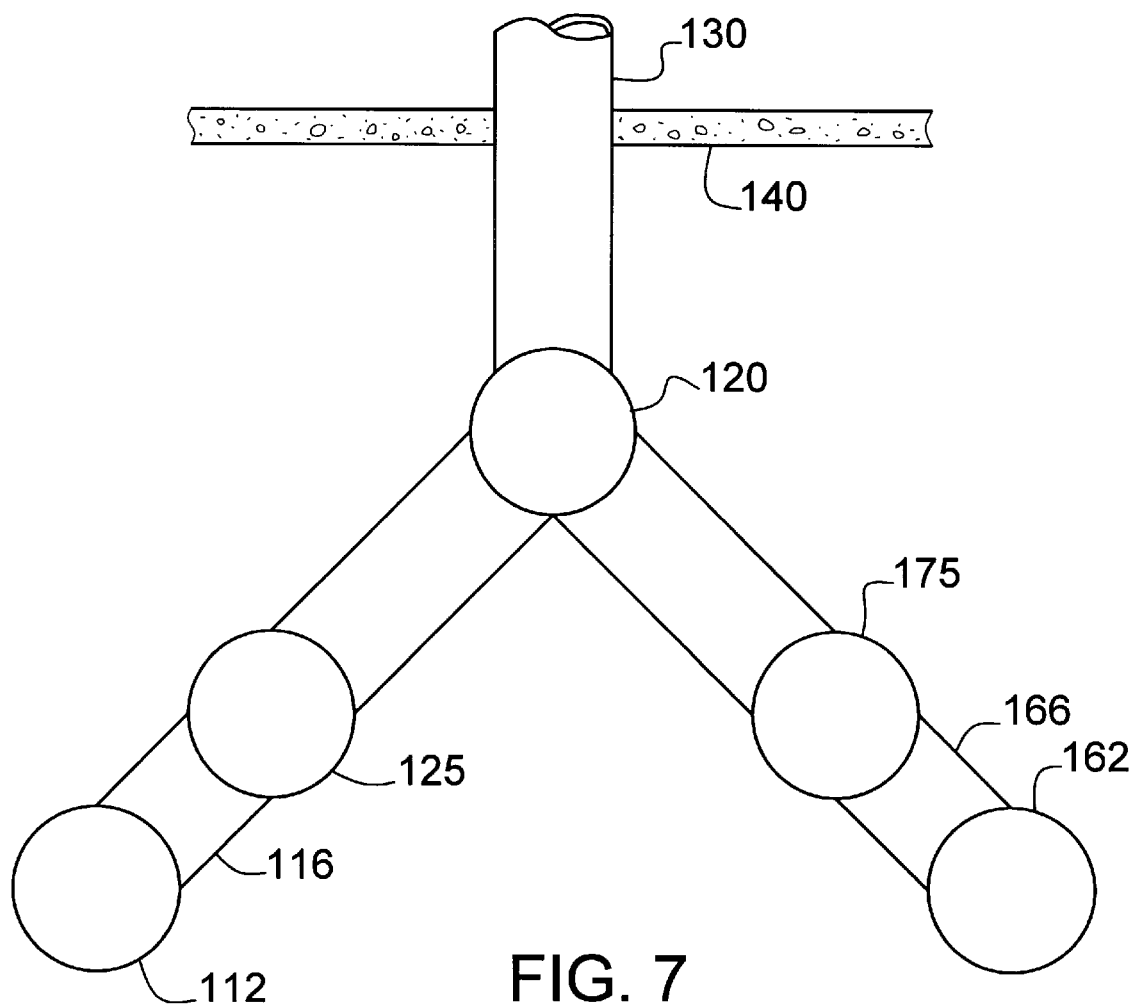
FIG. 7 is a top view of another test assembly of the present invention.

As shown in FIG. 7, another alternate embodiment of the present invention is shown in which a first testing line includes a first housing 112 having a bottom fluid entering inlet, not shown, and an outlet 116. The inlet is in flow communication with a waste water treatment effluent, such as a septic tank, and the first housing 112 includes a slotted filter or the like therein. The outlet 116 is in flow communication with a sample collection port 125. The sample collection port 125 is essentially the same as the one described in reference to sample collection port 25. The sample collection port 125 is constructed to receive a sample tube or a sample cup 108 as shown in FIG. 6. The sample collection port 125 is in flow communication with one of the inlets of a three-way valve 120, such as a BULL-RUN valve having two inlets and one outlet, the valve being open to only one inlet at a time. A second testing line is shown including a second housing 162 having an inlet, not shown, and an outlet 166 in flow communication with sample collection port 175. The sample collection port 175 is in flow communication with the other of the inlets to the three-way valve 120. The outlet of valve 120 is in flow communication with discharge outlet conduit 130 which extends through septic tank wall 140 and into a drain field or the like.

Although the present invention has been described with respect to details of only certain embodiments thereof, it is not intended that such details be limitations upon the scope of the present invention. It will be obvious to those skilled in the art that various modifications may be made to the described embodiments without departing from the spirit and scope of the invention as set forth in the claims as appended hereto.

What is claimed is:

1. A sampling assembly for waste water effluent comprising:
    a first flow line and a second flow line, each of the flow lines having an inlet in flow communication with said waste water effluent, each of said flow lines having an outlet, at least one of said flow lines having a housing with filter means therein;
    a first testing means disposed within said first flow line, said first testing means having a first sample collection port with a first valve means disposed to close off flow to said first sample port; and,
    a second testing means disposed within said second flow line, said second testing means having a second sample port with a second valve means disposed to close off flow to said second sample port.

2. The sampling assembly of claim 1, said first valve means being disposed between said first flow line inlet and said first sample port, said second valve means being disposed between said second flow line inlet and said second sample port.

3. The sampling assembly of claim 1, said first valve means being upstream of said first sample port and said second valve means being disposed upstream of said second sample port.

4. The sampling assembly of claim 3, said first valve means and said second valve means having separate inlets and one outlet, one of said separate inlets being in flow communication with said first sample port and another of said separate inlets being in flow communication with said second sample port.

5. The sampling assembly of claim 1, said first flow line having a first housing with a first filter means and said second flow line having a second housing with a second filter means.

6. The sampling assembly of claim 5, said first filter means being of one type of filter and said second filter means being a second type of filter.

7. The sampling assembly of claim 1, said first valve means and said second valve means being back flow valves.

8. The sampling assembly of claim 1, said first valve means and said second valve means being slide gate valves.

9. The sampling assembly of claim 1, said sample collection port including a sample tube inlet opening and a sample collection well.

10. The sampling assembly of claim 1, said sample collection port including a sample well with an opening in the top thereof and a removable cap over said opening in the top.

11. The sampling assembly of claim 1, each of said sample ports including a sample well, said sample well receiving a sample tube therein.

12. The sampling assembly of claim 1, each of said sample ports including a sample well, said sample well receiving a sample cup therein.

13. A method for sampling waste water effluent comprising the steps of:
    (a) placing a filter in at least one of a first testing line or a second testing line;
    (b) passing effluent through said first testing line including a first valve in an open condition and a first sample collection port;
    (c) removing all effluent from said first sample collection port;
    (d) opening said first valve for a preselected period of time;
    (e) closing said first valve;
    (f) removing all effluent from said first sample collection port;
    (g) opening a second valve in a second testing line;
    (h) passing effluent through said second testing line including said second valve and a second sample collection port;
    (i) closing said second valve;
    (j) removing all effluent from said second sample collection port;
    (k) opening said second valve for a preselected period of time;
    (l) closing said second valve;
    (m) removing all effluent from the second sample collection port; and,
    (n) opening said first valve; and,
    (o) determining selected chemical or physical data collected from effluent from said first sample collection port and from the second collection port and comparing said data.

14. The method of claim 13 including filtering effluent before passing said effluent through one of said first testing line or said second testing line.

15. The method of claim 13 including filtering effluent through one type of filter before passing said effluent through a first testing line and filtering separate effluent through a second type of filter before passing said effluent through said second testing line.

16. The method of claim 13, said removing effluent from said first and said second sample collection ports including vacuuming said effluent from said sample collection port.

17. The method of claim 13, said first sample port being downstream of said first valve, said second sample port being downstream of said second valve.

18. The method of claim 13, said determining selected chemical or physical data including determining solids concentration.

* * * * *